United States Patent [19]

Speidel

[11] Patent Number: 4,915,348

[45] Date of Patent: Apr. 10, 1990

[54] EXHAUST VALVE FOR BLOOD PRESSURE MEASURING APPARATUS

[75] Inventor: Blasius Speidel, Jungingen, Fed. Rep. of Germany

[73] Assignee: Speidel + Keller GmbH & Co. KG, Jungingen, Fed. Rep. of Germany

[21] Appl. No.: 298,851

[22] Filed: Jan. 18, 1989

Related U.S. Application Data

[63] Continuation of Ser. No. 115,508, Nov. 3, 1987, abandoned.

[30] Foreign Application Priority Data

Nov. 3, 1986 [DE] Fed. Rep. of Germany ....... 3637271

[51] Int. Cl.$^4$ .......................... F16K 1/38; F16K 31/50
[52] U.S. Cl. ..................................... 251/122; 251/273; 251/278; 251/321; 251/903
[58] Field of Search ............... 251/321, 273, 278, 120, 251/122, 903

[56] References Cited

U.S. PATENT DOCUMENTS

| 877,875 | 1/1908 | van Nostran | 251/273 |
| 1,268,316 | 6/1918 | Bergens | 251/121 |
| 2,452,956 | 11/1948 | Robins | 251/122 |
| 4,013,265 | 3/1977 | Speidel | 251/205 |
| 4,200,259 | 4/1980 | Ueda | 251/285 |

FOREIGN PATENT DOCUMENTS 8629328 11/1986 Fed. Rep. of Germany .
440372 5/1912 France .................. 251/278

Primary Examiner—Arnold Rosenthal
Attorney, Agent, or Firm—Foley & Lardner, Schwartz, Jeffery, Schwaab, Mack, Blumenthal & Evans

[57] ABSTRACT

An exhaust valve (10), particularly for a blood pressure measuring apparatus, comprising a valve seat (31) disposed along the course of an outlet channel in a valve housing (11) and oriented toward the pressure side of the valve. A valve body (25) having the form of a slender conical frustum arranged on the pressure side of the valve seat (31) cooperates with the valve seat. Valve body (25) is urged against the valve seat (31) by a closing spring (27). To facilitate controlled release of an elevated pressure contained by the valve, a screw cap (37) is arranged on the valve housing (11) along the axial projection line of the valve body (25), and the valve body (25) is connected to the screw cap (37) through a support bearing (43). A two-stage steep thread (44,45) is provided between the screw cap (37) and the valve housing (11).

11 Claims, 1 Drawing Sheet

EXHAUST VALVE FOR BLOOD PRESSURE MEASURING APPARATUS

This application is a continuation of application Ser. No. 07/115,508, filed Nov. 3, 1987, and now abandoned.

BACKGROUND OF THE INVENTION

Blood pressure measuring devices have a pressure system with a cuff which can be inflated, a pressure generating means, a pressure measuring device and an exhaust valve for decreasing the overpressure in the pressure system.

In one known exhaust valve, an outlet line which opens into free space is provided on a valve housing. In the course of the outlet line a valve seat is provided which is formed by a hollow frustoconical surface which annularly surrounds the outlet line. A conical valve body, which is guided so as to be movable back and forth relative to the valve seat along the longitudinal axis of the valve seat, cooperates with the valve seat. For this purpose, the valve body is connected to a screw cap which is adjustably guided by means of a thread concentrically to the longitudinal axis of the valve seat and consequently of the valve body. In order to close the pressure system as it is pumped up, the valve body is pressed by means of the screw cap against the valve seat through a screwing movement. Since a substantial transfer of force takes place through the threaded connection between the screw cap and the valve housing, the vertex angle of the conical surfaces of the valve seat and the valve body must not be too small in order to avoid binding or wedging of the valve body due to the friction between the conical surfaces. For this reason the vertex angle generally amounts to sixty degrees. Nevertheless, a clearly discernible binding friction or sticking arises between the two conical surfaces if the screw cap is closed with a certain degree of force to achieve a secure closing of the exhaust valve.

Due to the relatively oblique vertex angles of the two sealing surfaces, a relatively large change in cross section of the cross-sectional area which forms the outlet of the outlet valve occurs, even when there is only a very slight axial movement of the valve body with respect to the valve seat. Because at the beginning of the blood pressure measuring operation, the internal pressure in the pressure system has its highest value, a relatively high exhaust rate occurs when the outlet valve is opened which leads to a correspondingly rapid loss of pressure due to the limited volume of the pressure system. This rapid loss of pressure makes it more difficult to reliably determine the systolic blood pressure value, which must be read from the pressure measuring device as soon as the first sound of the Korotkoff flow arises in the artery underneath the point which was blocked off by the cuff at the higher overpressure which previously prevailed. The fine feel at the very beginning of the measurement operation is additionally made more difficult by the fact that the screw cap must be turned with a large initial twisting force due to the previously described sticking or frictional binding between the two sealing surfaces until the higher frictional holding force between the sealing surfaces is overcome and a lower sliding friction value is achieved. Since this transition from binding friction to sliding friction occurs abruptly, the higher initial twisting force applied by the fingers leads to the screw cap being turned beyond the point which would be necessary to have a fine "feel" of the release of pressure. Thus after this initial turn, the screw cap with the valve body must therefore first be turned back somewhat in the closure direction again in order to obtain the desired rate of escape for the air exiting from the pressure system.

In another known blood pressure measuring apparatus described in published German Patent Application No. DE-OS 21 28 295, the fine feel of the release of pressure even in the initial stage of the blood pressure measurement operation is made possible by using a relatively slender valve cone. This valve cone is actuated by means of a pivot key in order to achieve the larger adjusting movement which is required by the slender cone angle. Even though the actuation of the exhaust valve by means of the pivot key is significantly more convenient and a very fine feel of the reduction in pressure is possible because of the more favorable pressure release behavior of this valve, there are nonetheless persons who often use a blood pressure measuring device for professional reasons or other reasons and who do not want to switch from the familiar blood pressure measuring apparatus with the screw cap which they have used in the past to the other type of exhaust valve with the pivot key.

SUMMARY OF THE INVENTION

It is the object of the invention to improve the known type of exhaust valve with a screw cap in such a way that it is possible to release the pressure with a better fine feel than before.

This object is achieved by providing an exhaust valve comprising a valve housing including an outlet line opening into the ambient atmosphere and an annular valve seat arranged in the outlet line, a conical valve body which is movable relative to the valve seat at least substantially along the longitudinal axis of the valve seat, a screw cap for actuating the valve body which is axially adjustable along the longitudinal axis of the valve body by means of a thread having one threaded portion which is connected with the screw cap and another threaded portion which is connected with the valve housing, wherein:

the valve seat is oriented toward the interior of the valve housing, the valve body is formed as a slender conical frustum having a larger diameter portion which is oriented toward the interior of the valve housing, a closing spring is arranged in the valve housing, said spring being supported at one end against the valve housing and at the other end against the valve body and exerting a closing force in the direction toward the valve seat, said screw cap comprises a support bearing for the valve body against which the outwardly oriented end of the valve body is simultaneously rotatably and axially supported relative to the screw cap so as to be rotatable around the longitudinal axis of the screw cap, and said thread for effecting axial adjusting movements of the screw cap is formed as a two-stage steep thread.

Because the valve body is constructed as a slender conical frustum, when the valve body is moved axially, the change in the area of the outlet opening between the valve body and the valve seat is relatively small so that it is possible to regulate the release of air with a very fine feel, particularly in the initial portion of the opening movement of the valve body adjacent its closed position. This results in a corresponding fine feel for the reduction of pressure in the pressure system. Because the thread for axially displacing the screw cap is formed as a two-stage steep thread, the actuation path of the screw cap in the circumferential direction is reduced to such an extent that, despite the slender cone, convenient actuation of the screw cap is possible with only two fingers without one or several changes of position, and indeed without the fine feel of the release of air being reduced thereby. Because the valve body is arranged in the interior of the valve seat, i.e., on the side of the valve seat oriented toward the pressure system, and is firmly held against the valve seat in the closure direction by a closing spring, the outlet valve closes itself automatically in the absence of an opening force and indeed, under the force of the gas pressure alone which results from the overpressure in the pressure system and from the cross-sectional area of the valve body at the valve seat, as well as under the relatively small additional force of the closing spring in all cases. Due to the fact that the valve body can merely be lifted off the valve seat out of the closed position in the direction of opening and in the opposite sense cannot be forcibly pressed or drawn into the valve seat, the valve body is prevented from wedging itself fast in the valve seat, due to its slender form and small vertex angle, so solidly that it can only be moved out of this position again by applying large actuating forces. The required opening force for the valve cone thereby always remains the same in magnitude and in total is only relatively small. The binding of the valve body in the valve seat, which frequently arises in the known exhaust valve having an outwardly disposed valve body, thereby cannot occur because an incorrect actuation of the exhaust valve in this direction is not possible. Due to the fact that the screw cap is only connected to the valve body through a support bearing, the valve body does not undergo a rotational movement when the screw cap is actuated, either when the valve body moves outwardly until it seats against the valve seat or when the valve body moves inwardly until it is lifted from the valve seat.

Through constructing the exhaust valve with a valve body having a vertex angle of approximately six degrees and with a valve seat which is formed as an annular edge of a hollow cylindrical valve seat ring, a very high, fine feel in releasing pressure is achieved on the one hand and a high ease of use is assured on the other hand.

In constructing the exhaust valve with the average pitch angle of the steep thread being at most equal to, and preferably slightly less than, the friction angle ($\mu$) of the pair of materials from which the two threaded portions are made, the screw cap holds its position so that the force of the gas pressure acting from inside on the valve body and the closing force of the closing spring cannot move the screw cap outwardly. Consequently, once a position of the valve body is selected, it is then maintained even if the screw cap is not held in position by the user of the apparatus. A person using the blood pressure measuring apparatus is thereby relieved of the burden of having to monitor the maintaining of the rate at which the overpressure is released.

Through constructing the exhaust valve with the support bearing formed from a hollow conical bearing socket and from an annular edge of a mounting pin, which preferably is rounded off, very easy rotatability of the screw cap with respect to the valve body is achieved.

In constructing the exhaust valve with a bypass for the valve body sealing surface, preferably a bypass formed by at least one axially oriented recess, which extends from the unpressurized region of the valve body toward the pressurized region up to a point on the sealing surface which at normal opening displacement of the valve body is still located in a region of the valve seat where a throttle effect occurs, a rapid release of pressure is made possible in that after determining the lower blood pressure value, the valve body is brought by a relatively small additional rotation of the screw cap into the axial position in which the bypass is activated. Due to the significantly enlarged outlet area of the bypass, the remaining overpressure in the pressure system is thereafter released in the shortest possible time, so that very soon after completion of the actual measurement, the measuring cuff is sufficiently deflated and relaxed that it can be removed. This significantly reduces the length of time in which the cuff acts on the person whose blood pressure is being measured because with a normal outlet area the gas pressure approaches the zero value only asymptotically, so that the time interval until the pressure has been released to a sufficient degree that the cuff can be removed becomes very long. In addition, the person using the blood pressure measuring apparatus is also unburdened since the person can remove the cuff very soon after completion of the actual measuring operation and can turn, for example, to recording of the blood pressure values or to further examinations of persons whose blood pressures are to be measured.

As used herein, references to the "inward direction" refer to the direction toward the high pressure side of the valve (i.e., toward the left side in FIG. 1), and references to the "outward direction" refer to the direction toward the low pressure side of the valve (i.e., toward the right side in FIG. 1).

BRIEF DESCRIPTION OF THE DRAWINGS

In the following the invention will be explained in further detail with reference to two working embodiments illustrated in the drawings in which.

DETAILED DESCRIPTION OF PREFERRED EMBODIMENTS

Figure 1:
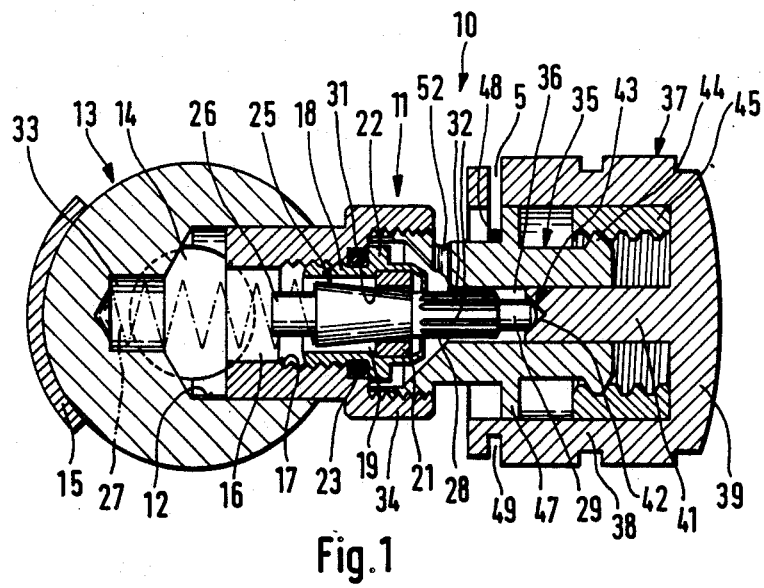
FIG. 1 shows a longitudinal section of a first embodiment of exhaust valve.

The exhaust valve 10 seen in FIG. 1 comprises a valve housing 11 which is positioned in a transverse bore 12 of a cylindrical base housing 13 of a blood pressure measuring apparatus, the remainder of which is not shown. This base housing 13 comprises an axial through opening 14 to which a pressure generating means, somewhat in the form of a rubber ball pump with a self-actuating inlet valve, is connected at one end of the base housing and a connecting line or hose to a measuring cuff and to a pressure measuring device of the blood pressure measuring apparatus is connected at the other end of which; all of which together form the blood pressure measuring apparatus. At one side of the pressure housing 13, a so-called spoon 15 is illustrated which extends parallel to the rubber ball of the rubber ball pump and makes the actuation of the rubber ball pump or squeeze pump easier.

The valve housing 11 is formed as a cylindrical body which is seated gas-tightly in the transverse bore. In general, the valve housing may be soldered in the bore, but it can also be screwed into the bore by means of a thread, with or without additional sealing means. In the interior of valve housing 11 there is a co-axially arranged outlet line 16 which, like the through opening 14, forms a part of the pressure system of the blood pressure measuring apparatus. In the vicinity of outlet line 16 there is an internal thread 17 on valve housing 11 in which a cylindrical valve seat support 18 provided with screw threads is screwed. This valve seat support 18 has an axial through opening 19 which has a recess in its outwardly oriented end region in which a valve seat ring 21 is inserted, which is held fast by a thin-walled axial extension of the valve seat support 18 in that this extension is inwardly bent over all the way around to a slight extent after insertion of the valve seat ring 21. On its outside, the valve seat support 18 has a flange 22 which presses a sealing ring 23 against a surrounding recess of valve housing 11 in order to provide a seal.

A valve body 25 is arranged co-axially to the valve seat ring 21. It is formed as a slender conical frustum, the vertex angle of which amounts to six degrees. The valve body 25 is a molded plastic body of polyamide material. A guide pin 26 for a closing spring 27 is formed at the inwardly oriented end of valve body 25, which is the end with the larger cone diameter. A substantially cylindrical extension 28 is connected at the outwardly positioned end of the conical frustum, which is the end that has the smaller diameter, and a mounting pin 29 with a reduced diameter is attached at the end of extension 28 which is remote from the conical frustum.

The valve seat ring 21 is formed as an annular cylinder, the inner annular edge of which oriented toward the base housing 13 forms the valve seat 31. The valve seat ring 21 is produced of polytetrafluoroethylene which in addition to good sliding properties also has a certain elasticity, by means of which the annular edge yields elastically when contacted by the valve body to such an extent that a small frustoconical contact surface is formed as the actual sealing surface.

The cylindrical extension 28 begins at a point on the valve body 25 which, when the valve body 25 is in the closed position (FIG. 1), is somewhat further removed from the valve seat 31 than corresponds to the normal opening displacement of the valve body. On the outside of the extension 28 there are a number of recesses 32 which are uniformly distributed around the circumference of the extension 28 and which have an approximately triangular cross-sectional configuration. The recesses 32 are oriented axially and open freely at the end of extension 28. The sum of the cross-sectional areas of recesses 32 forms an outlet area which supplements the open annular cross-sectional area which exists between the valve body 25 and the valve seat 31 when the valve body is moved into a certain open position. This supplemental outlet area is added to the normal cross-sectional area within a relatively small section of the path of movement of the valve body and thereby acts as a rapid release for the pressurized air in the pressure system of the blood pressure measuring apparatus.

In the projection line of valve housing 11 there is a cylindrical recess 33 in base housing 13 in which one end of the closing spring 27 is seated. It is guided in the radial direction therein by the surrounding wall of the recess and supported in the axial direction by the end surface of the recess. The other end of the closing spring is guided in the radial direction by guide pin 26 which is set back in comparison to the large diameter of the frustoconical form of valve body 25. Closing spring 26 is supported in the axial direction against the end face of valve body 25.

An annular collar 34 adjoins valve housing 11. Its interior width is larger than the outer diameter of flange 22 on valve seat support 18. The inner wall of collar 34 is provided with an internal thread. A guide body 35 is screwed into this thread. Guide body 35 is substantially cylindrical in form, and it has a cylindrical guide opening 36 concentric to its longitudinal axis, which coincides with the longitudinal axis of valve housing 11. The extension 28 extends partially into this guide opening 36. The guide opening 36 serves to guide a screw cap 37. Screw cap 37 comprises a jacket 38 which is closed at one end by a base 39. Base 39 is slightly curved on its outer surface. On its inner surface there is a guide pin 41 which is formed integrally with base 39 and jacket 38 coaxial to the longitudinal axis of screw cap 37. Guide pin 41 is so dimensioned with respect to the guide opening 36 that a movable seat is formed between the two parts.

The end face of guide pin 41 facing valve housing 11 is formed as a hollow conical bearing socket 42 against which the annular edge of the end of mounting pin 29 of valve body 25 is supported in the axial direction, whereby the mounting pin 29 is simultaneously guided in the radial direction. This annular edge can be lightly seized or lightly rounded in cross section. The bearing socket 42 and the mounting pin 29 together form a support bearing 43 for valve body 25. A threaded portion 44 is provided at the end of guide body 35 which faces away from valve housing 11. Threaded portion 44 is formed by a flange which is provided with an external thread. A threaded lining 45 in the form of an annular cylinder is fixedly inserted in the interior of jacket 38 of screw cap 37. This threaded lining is provided with an internal thread which mates with the external thread of threaded portion 44.

The screw cap 37 is provided in a conventional manner with means for preventing it from being screwed off. This comprises a flange 47 formed integrally with guide body 35 and a leaf spring 48. Flange 47 has an outer diameter which is only slightly smaller than the inner diameter of jacket 38. The leaf spring 48 is inserted in an annular groove 49 on the outer surface of jacket 38 in which it is securely held by means of its resilient ends. The jacket 38 is provided on one side with a slit 51 extending into the interior through which a straight longitudinal section of leaf spring 48 extends. Flange 47 is disposed on guide body 35 in the plane which is reached by leaf spring 48 when the screw cap 37 is screwed away from valve housing 11 far enough that, on the one hand, valve body 25 lies securely in contact with valve seat 31 and, on the other hand, mounting pin 29 is still not withdrawn out of bearing socket 42.

A lateral outlet opening 52 is provided on guide body 35 axially outside of valve seat support 18, through which the air flowing out between the valve seat 31 and the valve body, which has been lifted a greater or lesser distance off the valve seat, can escape into the ambient atmosphere.

Figure 2:
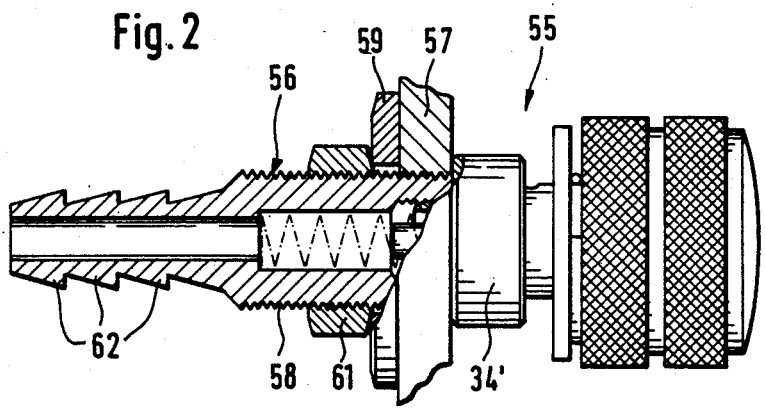
FIG. 2 shows a partial sectional view of a modified embodiment of an exhaust valve.

The exhaust valve 55 shown in FIG. 2 is modified in comparison with exhaust valve 10 only in respect to its connection with the blood pressure measuring apparatus. Its valve housing 56 is screwed onto a wall 57 of a housing of the alternate blood pressure measuring apparatus embodiment, which is not shown in other respects. For this purpose the valve housing 56 is provided with an external thread 58. The valve housing 56 extends through an opening in the wall 57 to such an extent that its collar 34' lies adjacent the exterior of wall 57. An underlying plate 59 is pushed onto housing 56 and a nut 61 is then screwed on from the direction of the interior of the housing. The outlet valve 55 is thereby firmly attached to the housing. The valve housing 56 adjacent external thread 58 is formed as a hose nipple 62 onto which a connecting hose can be pushed through which the exhaust valve 55 is connected with the remaining parts of the pressure system.

I claim:

1. An exhaust valve comprising:
   a valve housing defining an outlet channel with an annular valve seat arranged along the course of said outlet channel, said valve seat facing toward the interior of said valve housing;
   a conical valve body formed as a slender conical frustum having its larger diameter end oriented toward the interior of said valve housing and disposed in said outlet channel adjacent said valve seat so as to be axially movable into and out of contact with said valve seat, said conical valve body forming a gas-tight seal at the point of contact when it is in contact with said valve seat;
   a closing spring arranged in said valve housing having one end supported against the valve housing and its other end supported against the valve body and exerting a closing force on said valve body in the direction toward the valve seat; and
   a screw cap mounted by two-stage steep threads on said valve housing so as to move axially along said valve housing when turned, said screw cap contacting said valve body through a support bearing, which rotatably axially and radially supports the outwardly oriented end of the valve body, to move said valve body axially within said valve housing.

2. An exhaust valve comprising:
   a valve housing defining an outlet channel with an annular valve seat arranged along the course of said outlet channel, said valve seat facing toward the interior of said valve housing;
   a conical valve body formed as a slender conical frustum having its larger diameter end oriented toward the interior of said valve housing and disposed in said outlet channel adjacent said valve seat so as to be axially movable into and out of contact with said valve seat; wherein the valve body has a cone vertex angle of approximately six degrees, and the valve seat is formed by an inner annular edge of a hollow cylindrical valve seat ring;
   a closing spring arranged in said valve housing having one end supported against the valve housing and its other end supported against the valve body and exerting a closing force on said valve body in the direction toward the valve seat; and
   a screw cap mounted by two-stage steep threads on said valve housing so as to move axially along said valve housing when turned, said screw cap contacting said valve body through a support bearing, which rotatably axially and radially supports the outwardly oriented end of the valve body, to move said valve body axially within said valve housing.

3. An exhaust valve according to claim 2, wherein the valve seat ring is lightly gripped.

4. An exhaust valve according to claim 1, wherein the average pitch angle of said steep thread is not greater than the friction angle ($\mu$) of the pair of materials from which the two threaded portions are made.

5. An exhaust valve according to claim 4, wherein said thread comprises one threaded portion on said screw cap and a second threaded portion on said valve housing, and the average pitch angle of the steep thread is slightly less than the friction angle ($\mu$) of the pair of materials from which the two threaded portions are made.

6. An exhaust valve according to claim 1, wherein said support bearing is formed by a free end of a mounting pin received in a hollow conical bearing socket.

7. An exhaust valve according to claim 6, wherein the end of said mounting pin is rounded off.

8. An exhaust valve according to claim 6, wherein said bearing socket is arranged on said screw cap; said mounting pin is arranged on said valve body and has a smaller diameter than said valve body.

9. An exhaust valve according to claim 1, wherein said valve body is provided with at least one bypass extending from an unpressurized region of the valve toward a pressurized region up to a point on said valve body where a throttle effect occurs between said valve body and said valve seat when said valve body is in a normal open position.

10. An exhaust valve according to claim 9, wherein each said bypass comprises an axially extending recess in the outer surface of said valve body.

11. An exhaust valve according to claim 10, wherein a plurality of bypass recesses are uniformly distributed around the circumference of said valve body.

* * * * *